United States Patent [19]

Miller

[11] Patent Number: 5,277,030
[45] Date of Patent: Jan. 11, 1994

[54] PRECONDITIONING STAND FOR COOLING PROBE

[75] Inventor: William R. Miller, Skaneateles Falls, N.Y.

[73] Assignee: Welch Allyn, Inc., Skaneateles Falls, N.Y.

[21] Appl. No.: 9,314

[22] Filed: Jan. 22, 1993

[51] Int. Cl.$^5$ .................. F25B 21/02; A61B 17/36
[52] U.S. Cl. ........................ 62/3.2; 621/236; 621/530; 621/324.3; 607/104
[58] Field of Search .............. 62/3.2, 3.3, 3.7, 236, 62/238.2, 293, 529, 530, 3.6, 3.62, 324.3; 128/399, 403

[56] References Cited

U.S. PATENT DOCUMENTS

| | | | |
|---|---|---|---|
| 3,064,440 | 11/1962 | Waller | 62/3.3 |
| 3,127,749 | 4/1964 | Bergvall et al. | 62/3.2 |
| 3,133,539 | 5/1964 | Eidus | 128/399 |
| 3,289,749 | 12/1966 | Crump | 165/48 |
| 3,971,229 | 7/1976 | Privas | 62/3 |
| 4,308,013 | 12/1981 | Major | 433/32 |
| 4,519,389 | 5/1985 | Gudkin et al. | 128/303.1 |
| 4,612,772 | 9/1986 | Jones | 62/3.6 |
| 4,711,099 | 12/1987 | Polan et al. | 62/457 |
| 4,991,399 | 2/1991 | Bourcier et al. | 62/3.3 |
| 5,058,396 | 10/1991 | Faiola | 62/457.2 |

Primary Examiner—Albert J. Makay
Assistant Examiner—William C. Doerrler
Attorney, Agent, or Firm—Wall and Roehrig

[57] ABSTRACT

A cooling stand for preconditioning a cooling probe containing a refrigerant that includes a well in which the probe is removably mounted against a heat transfer interface and a heat pump in the stand for removing energy from a thermal storage material to pre-cool the probe prior to use. In one embodiment of the invention, a cold reservoir containing a phase change material is mounted in the stand which acts as a heat sink for the heat pump. The heat pump is reversed when the probe is removed to cool the reservoir.

15 Claims, 3 Drawing Sheets

PRECONDITIONING STAND FOR COOLING PROBE

BACKGROUND OF THE INVENTION

This invention relates to a cold stand for charging a removable, hand-held, cooling probe or similar portable cooling device in order to precondition it for use at a remote location.

One type of hand-held, cooling probe is shown in U.S. Pat. No. 5,058,396 to Faiola. A probe such as this is a simple, hollow wand containing a refrigerant that is placed in thermal contact with a body to be chilled. The refrigerant may be a liquid, a solid or a phase change material that can change from a liquid state to a frozen state. The latent heat of fusion is used in this latter instance to produce rapid chilling of the body being acted upon. Because this probe does not contain components, it is referred to herein as a passive probe.

Another example of a hand-held, cooling probe is disclosed in U.S. Pat. No. 3,133,539 to Eidus. In this case, the probe is used for medical purposes to treat skin lesions such as warts and the like. The probe contains a thermoelectric heat pump that employs the Peltier Effect at its proximal end and the hot junction of the heat pump is in contact with a heat sink in the form of a reservoir containing water or other suitable material. A tip is removably mounted in the proximal end of the probe in thermal contact with the cold junction of the heat pump. The tip is thermally conductive so that it will rapidly pull heat from the contacted body through the heat pump to produce rapid freezing. The heat energy is ultimately rejected by the heat pump into the reservoir. This type of probe is referred to herein as an active probe.

In U.S. Pat. No. 3,971,229 to Privas there is described another active, hand-held, medical probe that also contains a thermoelectric heat pump at one end thereof that is capable of attaining relatively low temperatures at its cold junction. The probe also contains a rechargeable battery for driving the heat pump. A probe stand is also provided which electrically connects the probe to an outside source of electrical power. When the probe is in the stand, the battery is recharged and the heat pump is controlled to operate at a desired operating level by the stand control electronics.

Although the probes such as this are predominantly used for chilling below the heat sink temperature, a switching mechanism allows the current to the heat pump to be reversed so that the probe can also be used for heating above the heat sink temperature. When in a chilling mode, heat is rejected by the heat pump into a heat sink and carried away to ambient by a fan.

One problem faced by those using hand-held probes of this nature is that of preconditioning the probe to perform its intended task. Although some stands, such as that disclosed by Privas, are capable of providing electrical power to the probe, none of these stands have the ability to deliver or accept thermal energy to or from the probe.

SUMMARY OF THE INVENTION

It is therefore an object of the present invention to improve hand-held cooling probes or similar devices.

It is a further object of the present invention to provide a stand for a cooling probe that is capable of providing cooling to a probe mounted in the stand.

A still further object of the invention is to provide a cooling stand for a hand-held cooling probe.

Another object of the present invention is to provide a cooling stand for a cooling probe that will minimize the forming of condensate on the stand surfaces when the probe is recharging or when the probe is removed from the stand.

Yet another object of the present invention is to precondition a hand-held, cooling probe both electrically and thermally so that the probe can be used immediately upon its removal from the stand and be quickly recharged when it is returned to the stand.

These and other objects of the present invention are attained by means of a cooling stand for preconditioning a handheld, cooling probe that includes a housing having a well for removably containing a probe therein. A heat transfer surface is positioned in the well that thermally communicates with a heat pump mounted in the stand. Electrical circuitry is also included in the stand to provide power to the stand's heat pump and auxiliary power to the probe, if required.

BRIEF DESCRIPTION OF THE DRAWINGS

For a better understanding of these and other objects of the invention, reference will be made to the following detailed description of the invention which is to be read in conjunction with the accompanying drawings, wherein.

DESCRIPTION OF THE INVENTION

Figure 1:
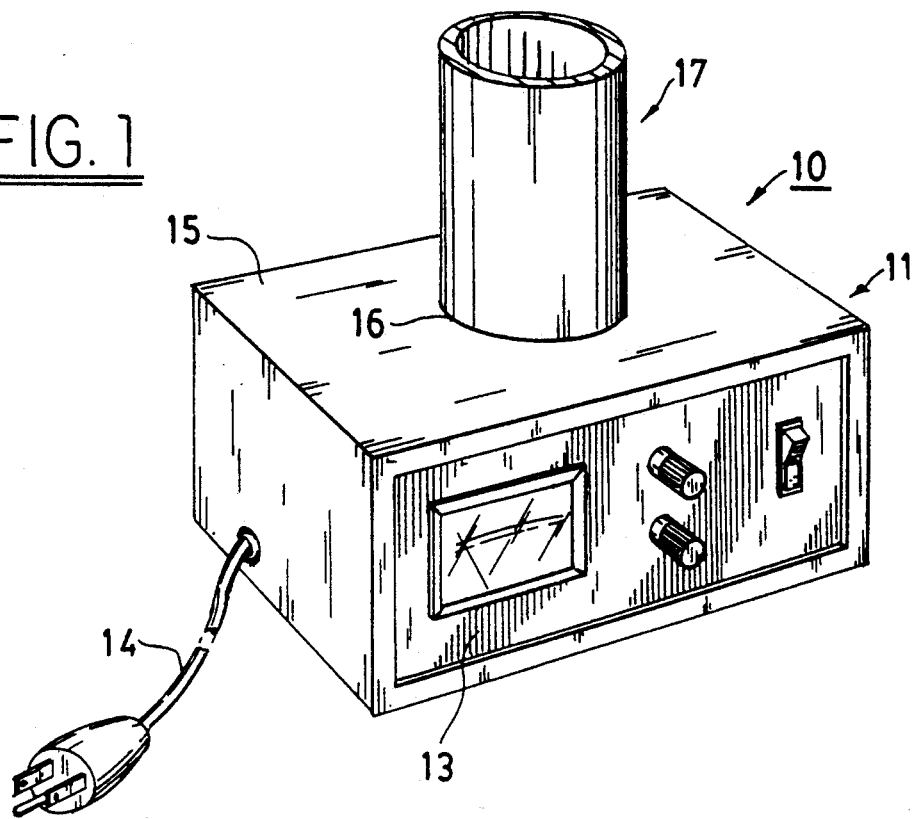
FIG. 1 is a perspective view of a cooling stand embodying the teachings of the present invention showing a hand-held, cooling probe mounted therein.

Turning now initially to FIG. 1 of the drawings, there is shown a cooling stand 10 embodying the teachings of the present invention. The stand includes a rectangular-shaped housing 11 having a control panel 13 mounted on its front face. The control panel configuration may vary depending upon whether the stand is utilized to precondition an active or a passive probe. For purposes of this disclosure, an active probe is one that includes a reservoir containing a thermal storage material and a heat pump for moving energy into and out of the reservoir. A passive probe is one having a reservoir containing a thermal storage material but does not include a heat pump. Similarly, in this instance, the thermal storage material is one that will change its state from a liquid to a solid at a desired probe temperature. An electrical line 14 for connecting the stand to a conventional electrical outlet passes into the housing through one of its side walls. The top wall 15 of the housing contains an entrance 16 to a well into which is inserted a hand-held, cooling probe generally referenced 17. The probe is supported in an upright position with a portion of its casing being exposed to facilitate insertion and removal of the probe from the well. As noted above, the probe may be either an active or passive device.

Figure 2:
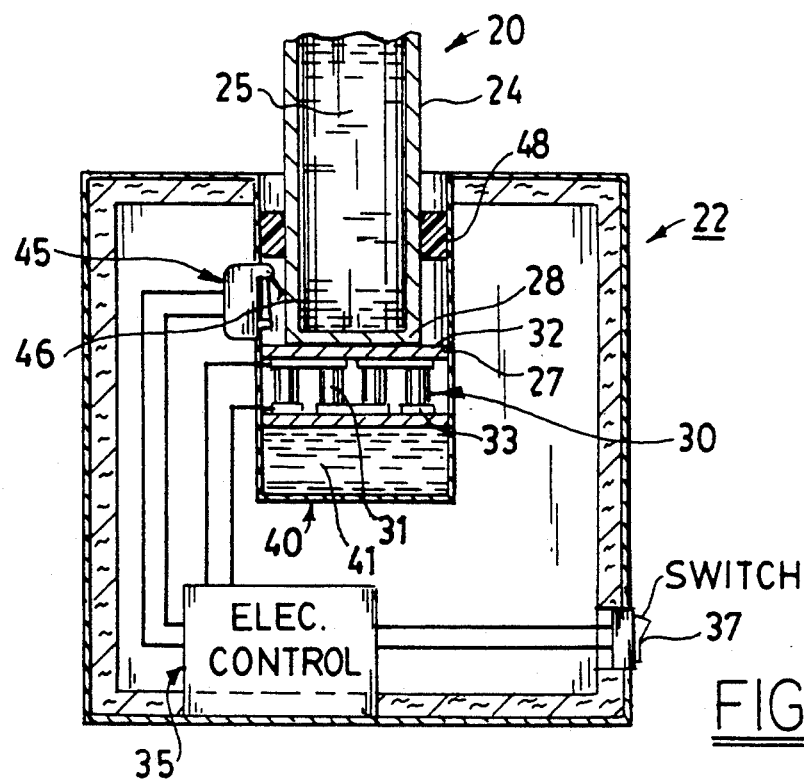
FIG. 2 is a schematic diagram showing a first embodiment of the stand being utilized to precondition a passive, cooling probe.

A passive probe 20 is illustrated in FIG. 2 contained within the well 21 of a stand 22. The passive probe includes an enclosed casing 24 which contains a quantity of thermal storage material 25. The material may be simply water or water containing an anti-freeze or chemical to lower its phase change temperature.

The bottom wall 27 of the well is a heat transfer surface formed of a metal such as copper or aluminum having high thermal conductivity upon which the proximal end 28 of the probe rests when the probe is mounted in the stand. Situated immediately adjacent to the heat transfer surface is a thermoelectric heat pump 30 that utilizes the Peltier Effect. Although a thermoelectric heat pump is employed herein, it should be clear to one skilled in the art that a mechanical heat pump may also be used without departing from the teachings of the present invention. The thermoelectric device is composed of a series of semi-conductor elements 31 that are mounted between a pair of junctions 32 and 33. Power is applied to the semi-conductor from an electrical unit 35. When current is passed through the semiconductor in one direction, one of the junctions will be heated and the other will be cooled. Reversing the flow of current changes the relationship of junctions wherein the hot junction becomes that cold junction and vise versa. As can be seen, the direction of heat flow through the heat pump can be quickly changed. A switch 37 is mounted in the control panel of the stand which controls the flow of electrical energy from an outside source to the electrical unit of the stand. A cold reservoir 40 is mounted below the heat pump and is in thermal communication with junction 33 of the heat pump. The cold reservoir contains a material 41 that changes from a liquid to a solid at a predetermined temperature.

A sensing switch 45 is mounted adjacent to the well with its sensing arm 46 being adapted to contact the outer surface of a probe situated therein. The sensing switch is coupled to an electrical unit and controls the direction of current flow to the heat pump. When a probe is inserted into the well as shown, current flows in a direction such that junction 32 acts as a cold junction and junction 33 acts as a hot junction. Accordingly, heat flows from the probe into the cold reservoir 40. Sufficient heat is rejected from the probe to place some or all of the probe thermal storage material 25 in a solid state. A penetrative gasket 48 is mounted in the well, which seals against a probe that is being preconditioned, to prevent moisture-laden air from entering the heat exchange region thus preventing condensate from developing in this region.

Upon removal of a probe from the well, the sensing switch is cycled thus reversing the function of the heat pump. At this time, junction 33 becomes the cold junction and junction 32 the hot junction. Energy from the cold reservoir is now rejected to ambient through the heat exchange surface 27. Sufficient energy is removed from the cold reservoir to place and hold the stand thermal storage material in a solid phase. As can be seen, this freezing of the phase change material is accomplished without the danger of condensate being formed in and around the well. To avoid heat gain into the reservoir, the inner surfaces of the stand are covered with a suitable insulating material.

Figure 3:
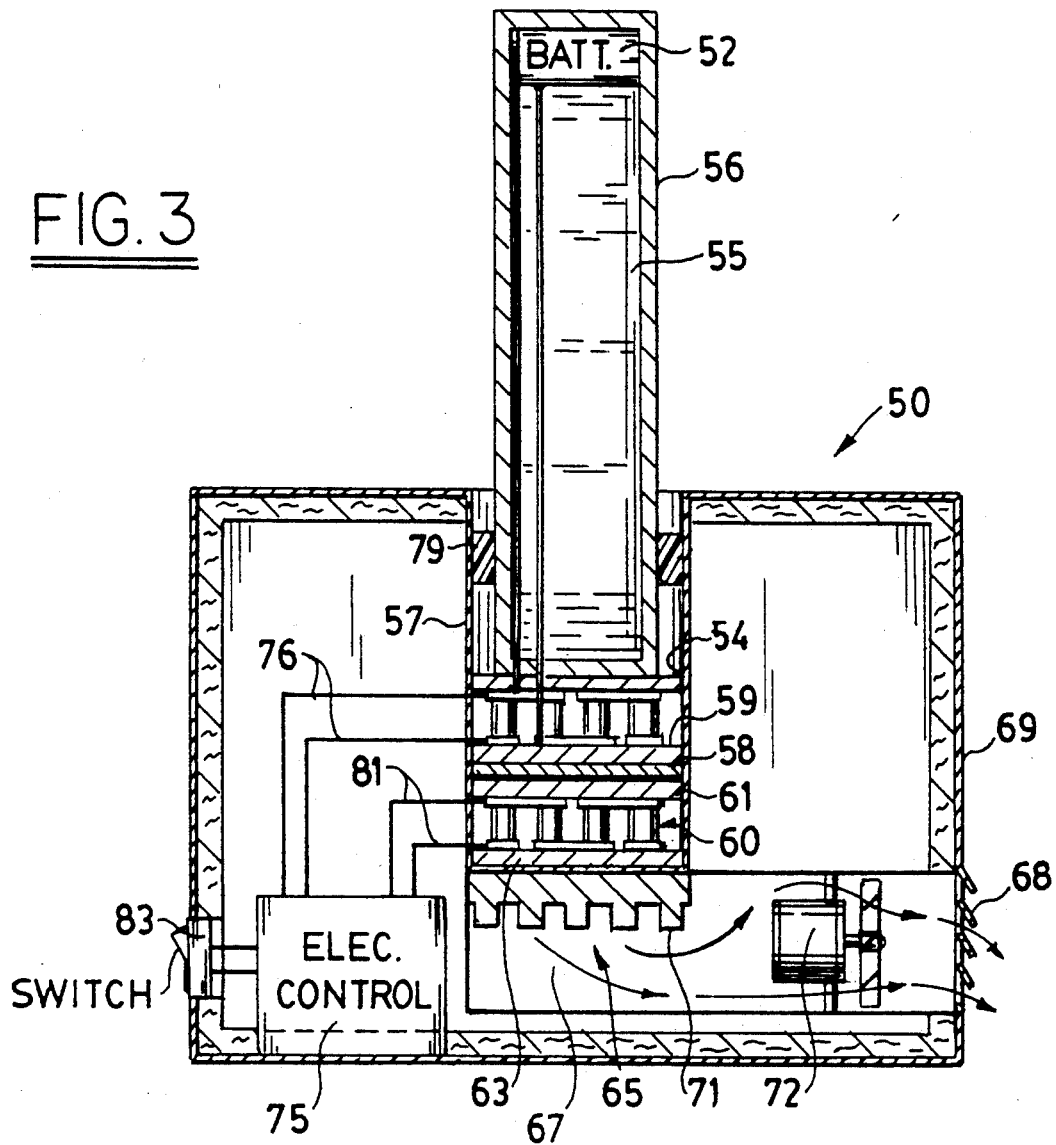
FIG. 3 is a schematic diagram showing a second embodiment of the stand that is being utilized to precondition an active, cooling probe.

FIG. 3 illustrates a second embodiment of a stand 50 for preconditioning an active probe 51 containing an internal battery 52 and an on-board thermoelectric heat pump 53. As explained in the previously noted Eidus patent, the probe may also include a removable tip which may be removed when the probe is inserted into the stand as shown. A cold reservoir 55, containing water or any other suitable thermal storage material, is mounted in the probe housing 56 immediately behind the probe heat pump and thermally communicates with the upper junction 54 of the heat pump. As is evident, removing heat from the cold reservoir will precondition the probe to lower its temperature so that the on-board heat pump 53 can work more efficiently and rapidly once it is removed from the stand.

Here again, the stand includes a well 57 having a heat exchange surface 58 adapted to thermally communicate with the lower junction 59 of the probe heat pump. A stand heat pump 60 is mounted in the stand with the upper junction 61 thereof in thermal contact with the heat exchange surface. The lower junction 63 of the heat pump is in thermal contact with a metal heat sink 65 having high thermal conductivity. Heat sink 65 is located in an air duct 67 that terminates at a louvered opening 68 in one side wall 69 of the stand housing. The heat sink has fins 71 that extend into the duct to provide for an efficient exchange of heat between the heat sink and ambient. A motor driven fan 72 is mounted in the duct behind the louvered opening which operates to discharge heated air out of the housing.

An electrical unit 75 is mounted within the housing which is adapted to provide power to both heat pumps. Although not shown, lines 76—76 are equipped with sliding contacts that electrically couple the internal power unit to the probe when the probe is seated within the well. A penetrative gasket 79 is also mounted in the well which again seals against the probe to prevent condensation from building up in the well when a probe is being preconditioned. Lines 76—76 also provide a connection to the rechargeable battery contained within the probe. A second set of lines 81—81 connect the electrical unit to the internal heat pump 60. The electrical unit is connected to a remote source of power via switch 83.

In operation, when a probe is inserted into the well, both of the heat pumps are energized. The pumps are arranged so that they operate in series to draw energy out of the reservoir of the probe. The temperature of the probe thermal storage material is thus rapidly reduced to precondition the probe for utilization at a remote location. At the same time, the electrical unit of the stand recharges the probe battery which powers the probe when it is out of the stand. Heat drawn away from the probe reservoir is removed from the stand via the heat sink and the exhaust duct.

Figure 4:
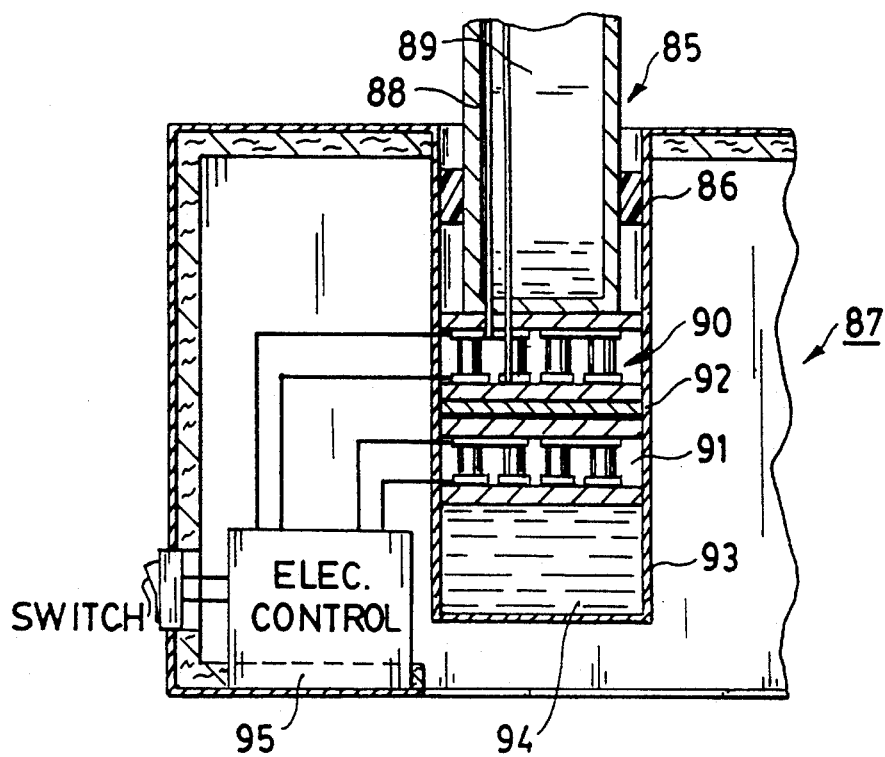
FIG. 4 is a schematic diagram showing a third embodiment of the stand for preconditioning an active probe.

A further embodiment of the invention will be described with reference to FIGS. 4 and 5. An active probe 85 is shown inserted within the well 86 of stand 87. The probe includes a reservoir 88 containing a first phase change material 89 and an on-board heat pump 90. A second heat pump 91 is mounted in the stand adjacent to a heat transfer surface 92. The stand heat pump is in thermal communication with a heat sink 93 which contains a second phase change material 94. An electrical control unit 95 is contained within the stand which, as explained above, is capable of powering both the on-board heat pump and the stand heat pump.

This arrangement, where both the probe and the stand have phase change material, heat sink and a heat pump, provides for maximum flexibility in the selection of operating temperatures and temperature differences. When a probe is in the stand and being preconditioned (cooled), efficiency is not of great concern since all the system components are being operated on line power. When the probe is in the portable mode, that is, removed from the stand, it is desirable to have as small a temperature difference as possible between the tip operating temperature and the onboard cold reservoir to minimize the work that the on-board heat pump is required to perform, thus minimizing battery drain.

It is also highly desirous to maintain the heat transfer surface of the stand above or close to freezing as possible when the probe is being charged to prevent or limit the amount of condensate on the heat transfer surface. Similarly, when the stand is in a reset mode, that is, with the probe removed, the heat transfer surface should be sufficiently above room ambient temperature to effectively pump heat out of the stand phase change reservoir.

Figure 5:
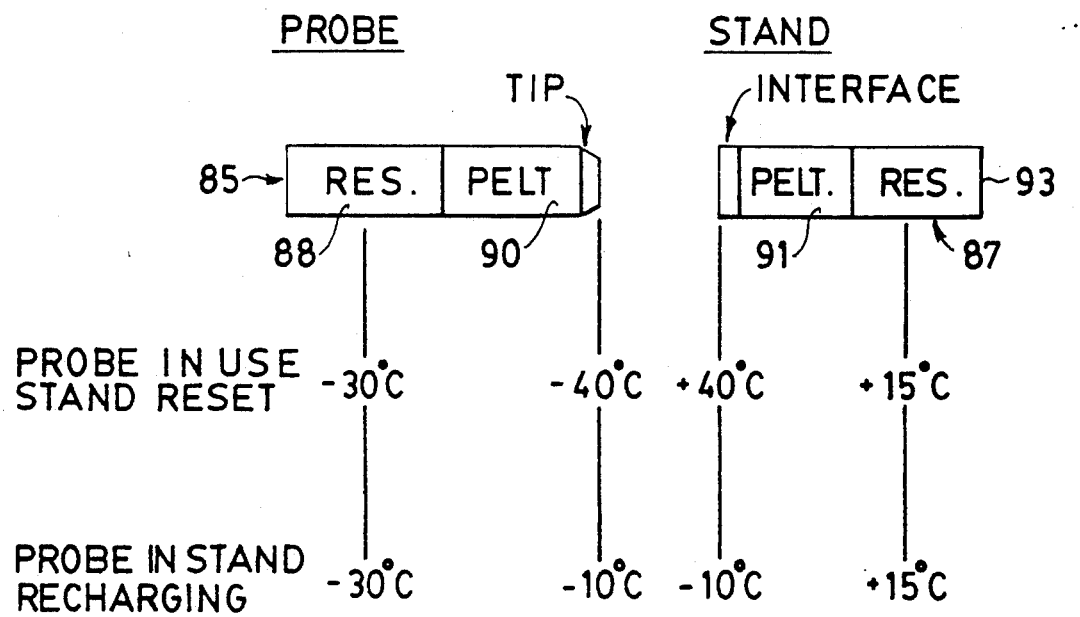
FIG. 5 is a diagram explaining the operation of the stand shown in FIG. 4.

A typical operational sequence of this type of system is illustrated in FIG. 5. Here the desired probe tip temperature, when in use, is about $-40°$ C. and the heat transfer surface i temperature of the stand must be about $+40°$ C. to reject heat from the stand reservoir to room ambient during the reset phase. The probe phase change material is designed with a change from liquid to solid state at a temperature of about $-30°$ C. As can be seen, the on-board heat pump has only to work against a $10°$ C. differential thus requiring use of relatively little battery power.

The stand phase change material transitions liquid to solid at about $+15°$ and its line powered heat pump is therefor working against a $25°$ C. differential rejecting heat into the ambient. This enables the stand to reset without any buildup of frost.

When the probe is docked in the stand, the functions of the heat pump are reversed and the on-board heat pump becomes line powered. The on-board heat pump now works against a $25°$ temperature differential to hold the heat transfer surface at about $-10°$ C. The stand heat pump is now pumping energy from the $-10°$ C. interface surface to the $+15°$ C. reservoir or at a reversed $25°$ C. differential.

While this invention has been described in detail with respect to preferred embodiments, it should be recognized that the invention is not limited to those embodiments. Rather, many modifications and variations would present themselves to those skilled in the art without departing from the scope and spirit of this invention, as defined in the appended claims.

I claim:

1. A cooling stand for preconditioning a cooling probe that includes
   a housing having a well for removably receiving a cooling probe therein, said probe containing a first quantity of thermal storage material,
   a heat transfer interface means in said well through which energy is transferred between the stand and the probe,
   a heat pump in said stand in thermal communication with the interface means whereby energy can be removed from the probe to precool the thermal storage material,
   a thermal reservoir, in thermal communication with said heat pump which contains a second quantity of thermal storage material to that energy removed from the probe is absorbed in this second quantity of thermal storage material, and
   means for reversing the heat pump when said probe is absent from said well for pumping heat from said second quantity of thermal storage material to an exterior environment.

2. A cooling stand for preconditioning a cooling probe that includes
   a housing having a well for removably receiving a cooling probe therein, said probe containing a first quantity of thermal storage material,
   a heat transfer interface means in said well through which energy is transferred between the stand and the probe,
   a heat pump in said stand in thermal communication with the interface means whereby energy can be removed from the probe to precool the thermal storage material,
   a cold reservoir in thermal contact with said heat pump and which contains a second quantity of thermal storage material so that thermal energy removed from the probe is absorbed in this second quantity, and
   sensing means for detecting the absence of a probe in said well and reversing the function of the heat pump to pump energy from the cold reservoir through the interface to ambient.

3. The cooling stand of claim 1 that further includes a gasket means in said well for sealing against a probe mounted in said well.

4. The cooling stand of claim 1 wherein said second thermal storage material is a phase change material that changes from a liquid to a solid within the operating temperature range of the heat pump.

5. The cooling stand of claim 1 wherein said heat pump is a thermoelectric pump utilizing the Peltier Effect.

6. The cooling stand of claim 5 wherein the thermoelectric heat pump has a first junction in contact with the stand interface means and a second junction in contact with the reservoir.

7. The cooling stand of claim 1 wherein said stand further includes a heat sink in thermal communication with the heat pump and means to cool said heat sink.

8. A cooling stand for preconditioning a cooling probe that includes
   housing having a well for removably receiving a cooling probe therein, said probe including a first cold reservoir containing a first thermal storage material and a first heat pump in thermal communication with said first reservoir so that energy can be pumped into and out of said reservoir,
   a heat transfer interface means in said well in thermal communication with said first heat pump and a second heat pump mounted in said stand,
   a second cold reservoir containing a second thermal storage material mounted in said stand in heat transfer communication with the second heat pump, and
   control means in said stand for operating both heat pumps independently.

9. The cooling stand of claim 8 wherein each thermal storage material is a phase change material that changes phase within the operating range of the heat pumps.

10. The cooling stand of claim 8 wherein said control means functions to pump heat from the first reservoir into the second reservoir when the probe is mounted in said stand and to pump heat from said second reservoir to ambient through said interface when the probe is removed from the stand.

11. The cooling stand of claim 8 wherein the heat pumps are thermoelectric heat pumps employing the Peltier Effect.

12. The cooling stand of claim 8 that further includes a gasket means in said well that seals against a probe mounted in said well.

13. The cooling stand of claim 1 wherein said first quantity of thermal storage material and said second quantity of thermal storage material comprise respective first and second phase change materials with respective different first and second phase transition temperatures.

14. The cooling stand of claim 13 wherein the first phase transition temperature is about −30° C.

15. The cooling stand of claim 13 wherein the second phase transition temperature is about +15° C.

* * * * *